(12) United States Patent
Liu et al.

(10) Patent No.: US 8,869,619 B2
(45) Date of Patent: *Oct. 28, 2014

(54) MULTIPURPOSE SENSOR FIXING DEVICE

(75) Inventors: Jianfeng Liu, Chengdu (CN); Heping Xie, Chengdu (CN); Jin Xu, Chengdu (CN)

(73) Assignee: Sichuan University (CN)

( * ) Notice: Subject to any disclaimer, the term of this patent is extended or adjusted under 35 U.S.C. 154(b) by 239 days.

This patent is subject to a terminal disclaimer.

(21) Appl. No.: 13/455,918

(22) Filed: Apr. 25, 2012

(65) Prior Publication Data

US 2012/0260734 A1  Oct. 18, 2012

Related U.S. Application Data

(63) Continuation of application No. 12/690,655, filed on Jan. 20, 2010, now Pat. No. 8,181,526.

(30) Foreign Application Priority Data

Jun. 15, 2009 (CN) .......................... 2009 1 0059594

(51) Int. Cl.
| | |
|---|---|
| *G01N 29/14* | (2006.01) |
| *G01N 29/22* | (2006.01) |
| *G01N 33/38* | (2006.01) |

(52) U.S. Cl.
CPC .............. *G01N 29/14* (2013.01); *G01N 29/223* (2013.01); *G01N 33/38* (2013.01); *G01N 2291/0232* (2013.01)
USPC ............................................. 73/587; 73/594

(58) Field of Classification Search
USPC .......................................... 73/587, 594, 801
See application file for complete search history.

(56) References Cited

U.S. PATENT DOCUMENTS

| | | | |
|---|---|---|---|
| 5,065,630 A | 11/1991 | Hadcock et al. | |
| 5,798,457 A | 8/1998 | Paulson | |
| 5,837,882 A | 11/1998 | Bacigalupo et al. | |
| 6,170,334 B1 | 1/2001 | Paulson | |
| 6,874,220 B1 | 4/2005 | Jones | |
| 8,181,525 B2 * | 5/2012 | Liu et al. .......................... | 73/587 |
| 8,181,526 B2 * | 5/2012 | Liu et al. .......................... | 73/587 |
| 2010/0313661 A1 | 12/2010 | Liu et al. | |
| 2010/0313662 A1 | 12/2010 | Liv et al. | |

FOREIGN PATENT DOCUMENTS

| | | |
|---|---|---|
| CN | 201413313 Y | 2/2010 |
| EP | 00040654761 | 3/1992 |
| JP | 2004205315 | 7/2004 |

* cited by examiner

*Primary Examiner* — J M Saint Surin
(74) *Attorney, Agent, or Firm* — Cantor Colburn LLP

(57) ABSTRACT

A multipurpose sensor fixing device includes a radial positioning mechanism, a supporting mechanism, a base, a mounting mechanism, and a parallelism adjusting member. The supporting mechanism comprises a main supporting arm and an auxiliary supporting arm, with one end of the auxiliary supporting arm connected to the main supporting arm and the other end comprising kink shaft members. The main supporting arm is connected to an end of the radial positioning mechanism to locate the auxiliary supporting arm at the inner side of the main supporting arm. The kink shaft member of the auxiliary supporting arm is inserted into a plughole of the base to form a revolute pair with the auxiliary supporting arm. The mounting mechanism is mounted at the base. The parallelism adjusting member is mounted on the main supporting arm.

20 Claims, 6 Drawing Sheets

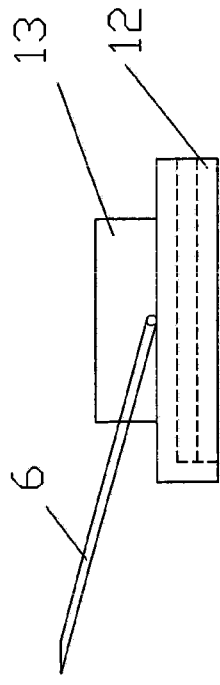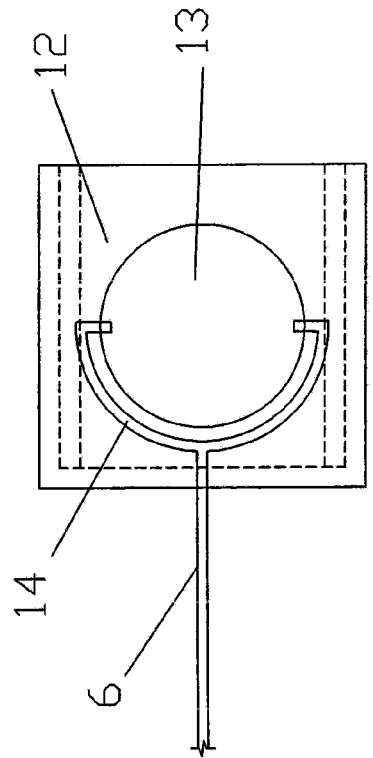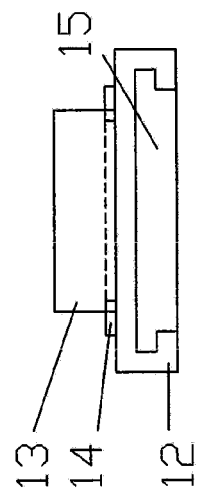
Figure 4
Figure 5
Figure 6

MULTIPURPOSE SENSOR FIXING DEVICE

RELATED APPLICATIONS

This application is a continuation of U.S. patent application Ser. No. 12/690,655, filed Jan. 20, 2010, which claims priority to Chinese Application No. 200910059594.2, filed Jun. 15, 2009. The entire disclosures of which are incorporated herein by reference.

FIELD OF THE INVENTION

The present invention relates to an acoustic emission test sensor fixing device used in columnar test piece experiment and test of materials such as rock and concrete.

BACKGROUND OF THE INVENTION

In rock mechanical experiments, when acoustic emission features of rock damage process and etc. are tested, the acoustic emission test sensors currently used do not have specific fixing devices, and two fixing methods of winding with rubber belt and fastening with bungee are commonly adopted in current experiments and tests. Acoustic emission test sensors generally have a diameter within the range of 5 mm to 15 mm and need to couple tested members using media, such as gel, butter, vaseline and etc. as a coupler, which result in that the fixing methods of winding with rubber belt and fastening with bungee are unable to ensure parallelism between the end face of the acoustic emission testing sensor and the coupling face of the tested member and the fine coupling between the end face of the acoustic emission test sensor and the tested member. Also, couplers such as butter, vaseline and etc, which may easily result in the adhesion reduction or failure of the rubber belt, and the rubber belt may easily form great binding on the acoustic emission test sensor during radial swelling and deforming of the tested member, so that it undertakes increasing force and is even damaged to some extent; for the fixing method of fastening by bungee, although the bungee is elongated by pulling during radial swelling and deforming of tested member and may deform to some extent, this fixing method may easily cause the acoustic emission test sensor to tumble, and thus it is difficult to ensure fine contact between the acoustic emission test sensor and the tested member. In addition, the above mentioned two fixing methods need to be performed before test pre-adding contact load and adjustment cannot be made during the experiment, and it is also difficult to accurately contraposition the acoustic emission test sensor. The above mentioned two fixing methods also have the following problems: (1) they can hardly ensure the consistency of force to the acoustic emission test sensor in the same batch of tested members and may easily form many pseudo signals, thus resulting in much difficulty to analysis and judgment of the testing result; and (2) they make the mounting of other deforming test sensors are very inconvenient.

SUMMARY OF THE INVENTION

The present invention may provide an acoustic emission test sensor fixing device, to meet the needs in acoustic emission test of the damage process of brittle materials such as rock and concrete, ensure fine contact between the acoustic emission test sensor and the tested member, and improve test efficiency and the accuracy and the truthfulness of the testing.

The acoustic emission test sensor fixing device according to the present invention comprises a radial positioning mechanism, supporting mechanisms, bases, acoustic emission test sensor mounting mechanisms, and parallelism adjusting members, wherein the supporting mechanisms, the bases, the acoustic emission test sensor mounting mechanisms, and the parallelism adjusting members are all in two sets; the supporting mechanism comprises a main supporting arm and an auxiliary supporting arm, and one end of the auxiliary supporting arm being fixedly connected to or hinged with the main supporting arm and the other end being provided with kink shaft members which are symmetrical about the auxiliary supporting arm, and when the auxiliary supporting arm is fixedly connected with the main supporting arm, the auxiliary supporting arm forms an acute angle or a right angle with respect to the main supporting arm, and the bases are provided with an plughole which form revolute pairs with the auxiliary supporting arm. The above assemblies or members are assembled as follows: the main supporting arms of the two sets of supporting mechanisms are connected to the two free ends of the radial positioning mechanism respectively in the way that the auxiliary supporting arms of the two sets of supporting mechanisms are located at the inner sides of the main supporting arms respectively and are arranged axis symmetrically with respect to the central line of the radial positioning mechanism, and the kink shaft members of the two auxiliary supporting arms are respectively inserted into the plugholes of the two bases to form revolute pairs, the two sets of acoustic emission test sensor mounting mechanisms are respectively mounted at the two bases, and the two sets of parallelism adjusting members are respectively mounted on the two main supporting arms and correspond to the positions of the bases.

Exemplary structures of the above assemblies constituting the acoustic emission test sensor fixing device according to the present invention are described as follows:

1. The radial positioning mechanism comprises two elastomers and one screw, and the two elastomers are connected with rigid ends at respective one end respectively, each of said rigid ends is provided with a screw hole matching the screw, and the screw forms screw pairs with the screw holes in the two rigid ends respectively; or the radial positioning mechanism only consists of elastomers.

2. The bases consists of a pedestal with a slot provided therein and a bulge on the pedestal, and the bulge is fixedly connected with or forms a one-piece structure with the pedestal, and the plugholes which form the revolute pairs with the auxiliary supporting arm are provided within the bulge.

3. Corresponding to the structure of the bases, the acoustic emission test sensor mounting mechanism comprises a plugboard matching the slot in the bases, an acoustic emission test sensor mounting member and an acoustic emission test sensor fixing member; the plugboard is provided with a screw hole or a fixing buckle for fixing the plugboard, and is inserted into the slot of the bases and fixed with the bases by a bolt or the fixing buckle; the acoustic emission test sensor mounting member is a cylinder provided with a gap therein and is fixedly connected with or forms a one-piece structure with the plugboard, with its inner diameter matching the outer diameter of an acoustic emission test sensor (during implementation, cylinders with different inner diameters can be made according to the acoustic emission test sensor, to form a series of cylinders meeting the demands of testing); the acoustic emission test sensor fixing member consists of a circular elastic plate provided with a gap and a fastening screw or a fixing buckle, when the acoustic emission test sensor is mounted within the cylinder provided with a gap, the circular elastic plate provided with a gap is put around the gap section of the cylinder, and then the acoustic emission test sensor is fixed within the cylinder by a fastening screw or the fixing buckle.

4. The parallelism adjusting member consists of two screws, and the main supporting arm is provided with a screw hole matching the screw at the position corresponding to the position of the bases, and the parallelism of the bases are adjusted by the screw.

The using method for the acoustic emission test sensor fixing device according to the present invention is described as follows:

1. Determine the number of the acoustic emission test sensors and the mounting position thereof at the tested member according to the shape of the tested member and the object of the experiment test, and mount the acoustic emission test sensor within the acoustic emission test sensor fixing device;
2. Place the tested member between upper and lower loading press heads of a testing machine, place the acoustic emission test sensors mounted within respective acoustic emission test sensor fixing devices on two sides of different portions of the tested member to be tested respectively, and attach the acoustic emission test sensors to the tested member tightly via the radial positioning mechanism; and
3. Rotate the bases so that the end face of the acoustic emission test sensor mounted in the acoustic emission test sensor fixing device is substantially parallel to the coupling surface portion of the tested member, and then adjust the end face of the acoustic emission test sensor via the parallelism adjusting member so that it is substantially parallel to the coupling surface of the tested member.

Upon conformity of mounting and adjusting of the acoustic emission test sensors with requirements, the test piece that needs to be tested can be tested according to a predetermined experiment and test solution.

The present invention realizes the following advantageous effects:

1. The acoustic emission test sensor fixing device according to the present invention is convenient in use, and it can also attach the acoustic emission test sensors tightly to the tested member during the whole testing process and keep the end face of the acoustic emission test sensors mounted in the acoustic emission test sensor fixing device parallel to the coupling surface of the tested member, thereby ensuring the truthfulness of the testing result and improving the accuracy of the testing result.
2. As the radial positioning mechanism comprises elastic members, when the tested member swells radially in the experiment, force of the acoustic emission test sensor will not increase, which could easily ensure force consistency of the acoustic emission test sensor during testing for the same batch of tested members, thereby lowering the influence of the pseudo signals on the test result and also improving the life of the acoustic emission test sensor.
3. The acoustic emission test sensor fixing device according to the present invention makes it convenient to arrange the acoustic emission test sensor at any position on the surface of the tested member, where other deforming test sensors can be arranged at the same time, so as to obtain more different testing information of the tested member during the same testing process.
4. Using the acoustic emission test sensor fixing device according to the present invention, the acoustic emission test sensor can be mounted at any period of time before or after pre-adding contact load to the tested member, and the position of the acoustic emission test sensor can also be adjusted during the experiment.

BRIEF DESCRIPTION OF THE DRAWINGS

FIG. 4 is schematic view illustrating a structure of the bases in the acoustic emission test sensor fixing device according to the present invention and an assembling of the bases and the auxiliary supporting arm;

FIG. 5 is a top view of FIG. 4;

FIG. 6 is a right view of FIG. 4;

In the figures: 1—screw, 2—rigid end, 3—arc elastomer, 4—main supporting arm, 5—parallelism adjusting member, 6—auxiliary supporting arm, 7—bases, 8—acoustic emission test sensor mounting mechanism, 9—acoustic emission test sensor, 10—the tested member, 11—semicircular elastomer, 12—pedestal, 13—bulge, 14—kink shaft member, 15—slot, 16—plugboard, 17—cylinder with gap, 18—circular elastic plate with gap, 19—sensor fastening screw, 20—plugboard fixing screw hole, 21—plugboard fixing buckle, and 22—sensor fixing buckle.

DETAILED DESCRIPTION OF THE INVENTION

The specific structure of the acoustic emission test sensor fixing device according to the present invention will be further illustrated hereinafter with reference to the accompanying drawings.

Embodiment 1

Figure 1:
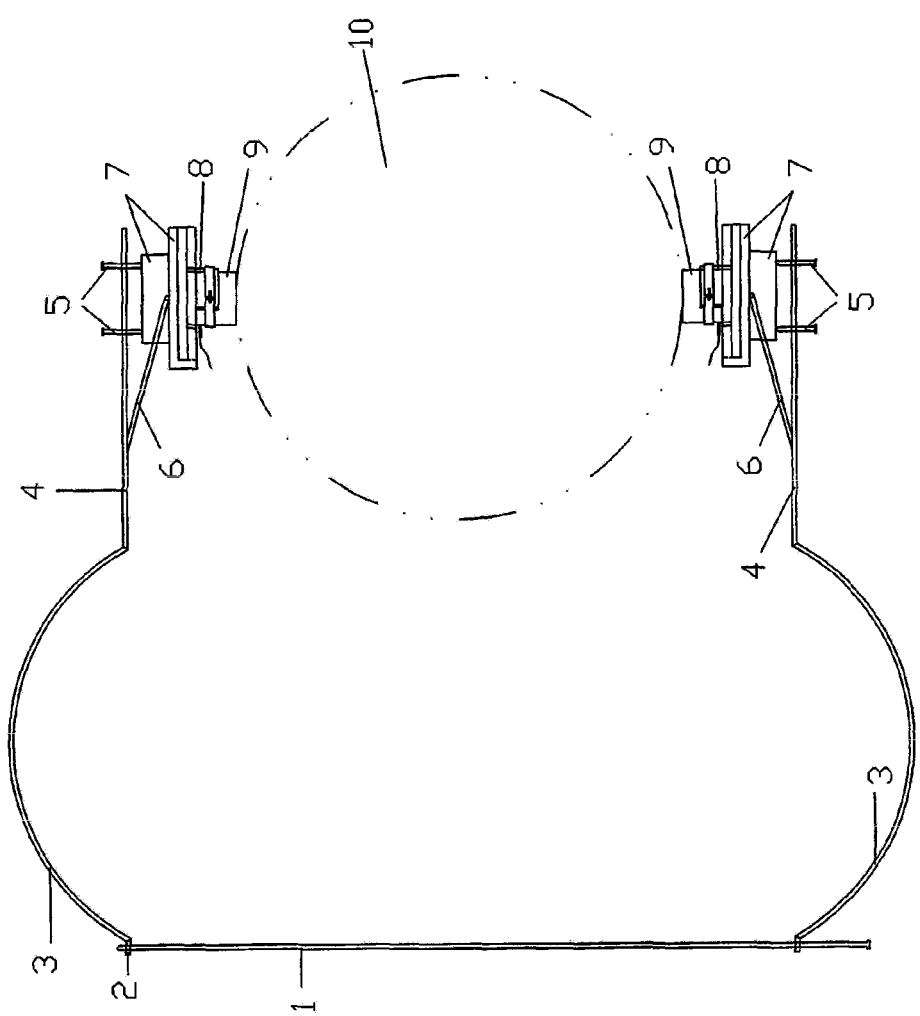
FIG. 1 is a schematic view illustrating a first structure of the acoustic emission test sensor fixing device according to the present invention.

In this embodiment, the structure of the acoustic emission test sensor is shown in FIG. 1, which comprising radial positioning mechanism, supporting mechanisms, bases 7, acoustic emission test sensor mounting mechanisms 8, and parallelism adjusting members 5, wherein the supporting mechanisms, the bases, the acoustic emission test sensor mounting mechanisms, and the parallelism adjusting members are all in two sets.

Figure 7:
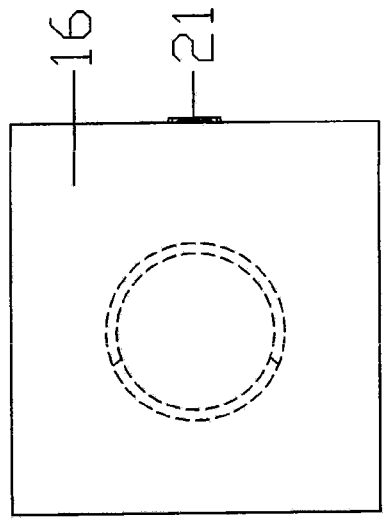
FIG. 7 is a schematic view illustrating a structure of the acoustic emission test sensor mounting mechanism in the acoustic emission test sensor fixing device according to the present invention.
Figure 8:
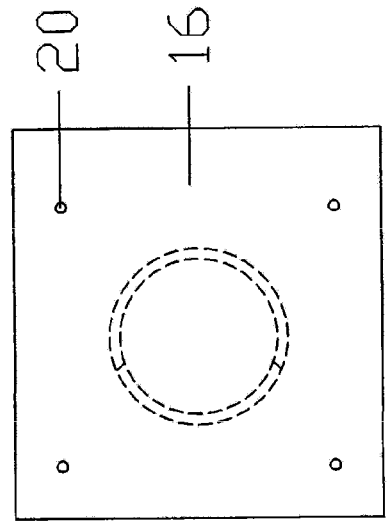
FIG. 8 is a top view of FIG. 7.

The radial positioning mechanism, as shown in FIG. 1, comprises two arc elastomers 3 and one screw 1, and the two arc elastomers are respectively connected with rigid ends 2 at respective one end, each of said rigid ends is provided with a screw hole matching the screw, and the screw forms screw pairs with the screw holes in the two rigid ends. The supporting mechanism, as shown in FIG. 1, comprises main supporting arm 4 and auxiliary supporting arm 6; the main supporting arms 4 are made of nickel titanium alloy and has a rectangular cross section, and are provided with two screw holes with interval there between at the position corresponding to the position of the bases; the auxiliary supporting arms 6 are made of nickel titanium alloy and has a rectangular cross section, with its one end fixed on the main supporting arm by threaded connection and forming an angle of 10° with the main supporting arm, and the other end is provided with kink shaft members 14, said kink shaft members, as shown in FIG. 5, consist of a semicircular shaft handle and two kink shafts provided on the end portions of the shaft handle which are symmetrical about and perpendicular to the auxiliary supporting arm, and are in threaded connection with the shaft handle. The bases 7, as shown in FIGS. 4, 5 and 6, consists of a pedestal 12 and a columnar bulge 13 on the pedestal, and the column bulge and the pedestal form a one-piece structure made of nickel titanium alloy, the pedestal is provided with a slot 15 therein, and the columnar bulge is provided with plugholes at the lower portion which matches the kink shafts on the auxiliary supporting arms 6. The acoustic emission test sensor mounting mechanism 8, as shown in FIGS. 7 and 8, comprises a plugboard 16 matching the slot in the bases, a cylinder 17 provided with a gap, a circular elastic plate 18 provided with a gap and a fastening screw 19, and the plugboard 16 is provided therein with four screw holes 20 for fixing the plugboard, the cylinder 17 is fixedly connected with the plugboard 16 at the end without a gap, and the end thereof with the gap is a free end, the circular elastic plate 18 provided with the gap is put around the gap section of the cylinder, and the acoustic emission test sensor 9 is fixed within the cylinder 17 by the fastening screw 19. The parallelism adjusting member 5 consists of two screws.

The above assemblies and members are assembled as follows: the main supporting arms 4 of the two sets of supporting mechanisms are respectively connected to the two free ends of the two arc elastomers 3 of the radial positioning mechanism, in the way that the two auxiliary supporting arms 6 are respectively located at the inner sides of the main supporting arms and are arranged axis symmetrically with respect to the central line of the radial positioning mechanism; the kink shafts of the kink shaft member 14 of the two auxiliary supporting arms are inserted into the plugholes in the columnar bulges 13 of the two bases to form revolute pairs respectively (as shown in FIG. 5); the plugboard 16 of the two sets of acoustic emission test sensor mounting mechanisms are inserted into the slots 15 of the two bases respectively and are fixed by bolts; and the screws comprising of the two sets of parallelism adjusting members 5 are mounted in the screw holes provided in the two main supporting arms respectively.

Embodiment 2

Figure 2:
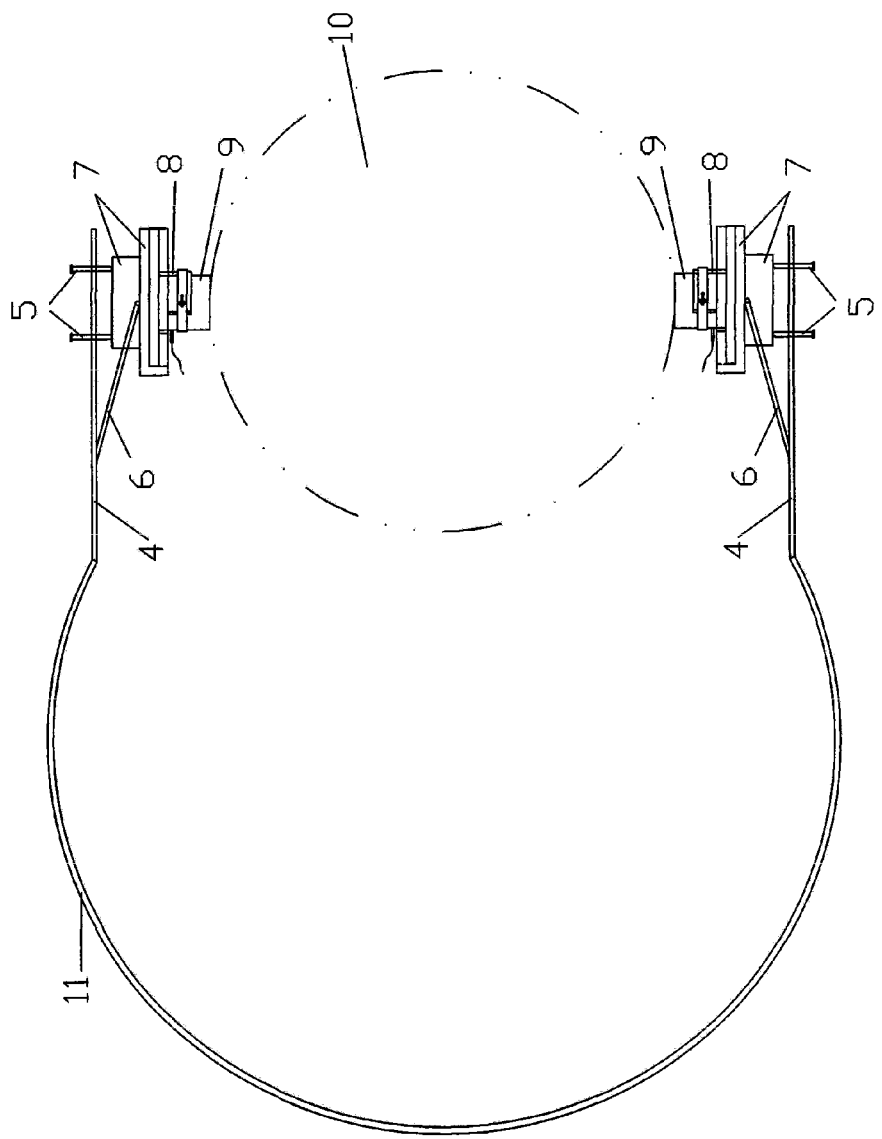
FIG. 2 is a schematic view illustrating a second structure of the acoustic emission test sensor fixing device according to the present invention.

In this embodiment, the structure of the acoustic emission test sensor fixing device is shown in FIG. 2, comprising a radial positioning mechanism, supporting mechanisms, bases 7, acoustic emission test sensor mounting mechanisms 8, and parallelism adjusting members 5, wherein the supporting mechanisms, the bases, the acoustic emission test sensor mounting mechanisms, and the parallelism adjusting members are all in two sets.

Figure 9:
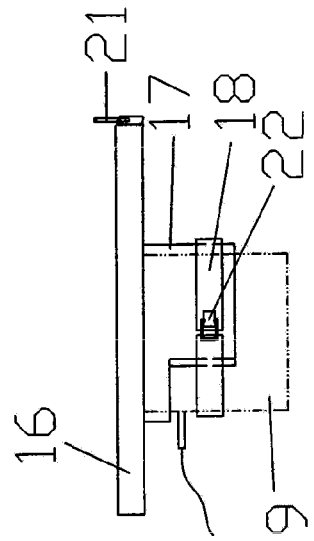
FIG. 9 is a schematic view illustrating another structure of the acoustic emission test sensor mounting mechanism in the acoustic emission test sensor fixing device according to the present invention.
Figure 10:
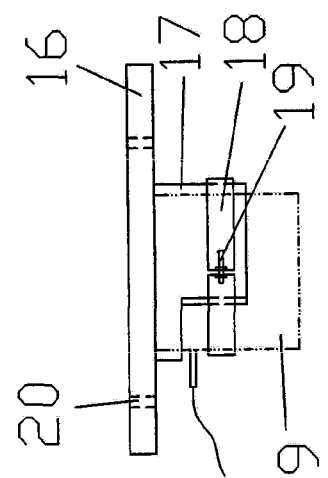
FIG. 10 is a top view of FIG. 9.
Figure 11:
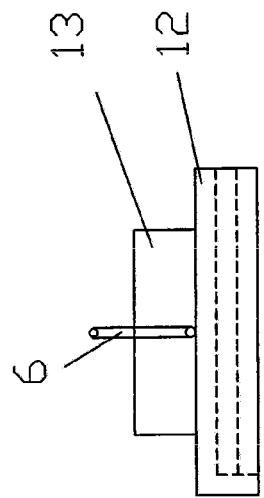
FIG. 11 is a schematic view illustrating another assembling of the bases and the auxiliary supporting arm in the acoustic emission test sensor fixing device according to the present invention.
Figure 12:
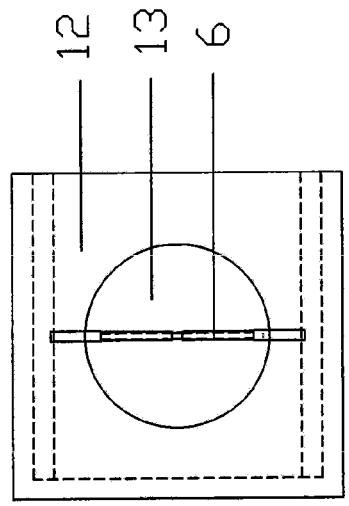
FIG. 12 is a top view of FIG. 11.
Figure 13:
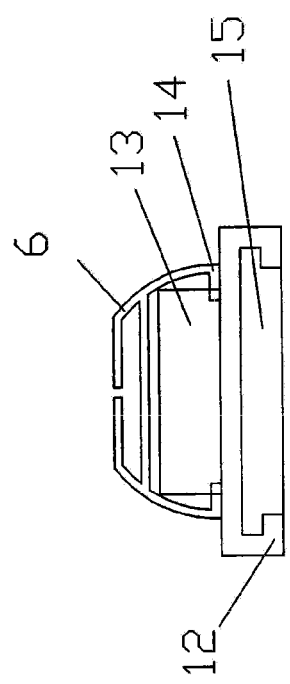
FIG. 13 is a right view of FIG. 11.

Different from embodiment 1, it is described in embodiment 2 that 1) the radial positioning mechanism is a semicircular elastomer 11 (as shown in FIG. 2); and 2) the acoustic emission test sensor mounting mechanism 8 is shown in FIGS. 9 and 10, wherein the plugboard 16 is provided with a fixing buckle 21 thereon, and when the plugboard 16 is inserted into the slot 15 which is in the base, it is fixed by the fixing buckle 21; the circular elastic plate 18 provided with the gap is put around the gap section of the cylinder, and the acoustic emission test sensor 9 is fixed within the cylinder 17 by the fixing buckle 22.

Embodiment 3

Figure 3:
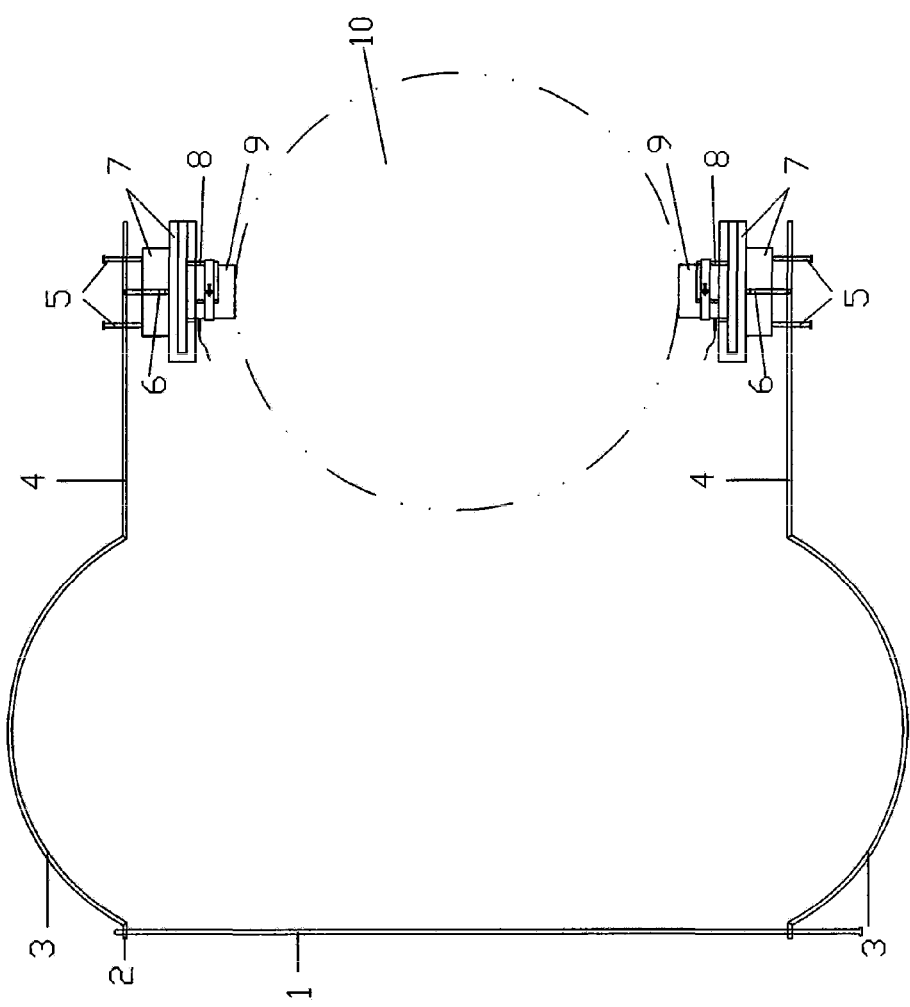
FIG. 3 is a schematic view illustrating a third structure of the acoustic emission test sensor fixing device according to the present invention.

In this embodiment, the structure of the acoustic emission test sensor fixing device is shown in FIG. 3, comprising a radial positioning mechanism, supporting mechanisms, bases 7, acoustic emission test sensor mounting mechanisms 8, and parallelism adjusting members 5, wherein the supporting mechanisms, the bases, the acoustic emission test sensor mounting mechanisms, and the parallelism adjusting members are all in two sets.

Different from embodiment 1, it is described in embodiment 3 that the auxiliary support arms 6 is in a "hook shape", and is provided with a screw fixedly connected with the main supporting arm 4 or kink shafts hinged with the main support arm 4 at the upper end, and is provided with the kink shaft member 14 at the lower end (as shown in FIG. 3), when the auxiliary supporting arm is fixedly connected with the main supporting arm, the angle between auxiliary supporting arm and the main supporting arm is right angle (as shown in FIG. 3), and when the auxiliary supporting arm is hinged with the main supporting arm, the kink shafts at the upper end of the auxiliary support arm are inserted into the plugholes provided within the main supporting arm.

What is claimed is:

1. An acoustic emission test sensor fixing device, comprising:
a radial positioning mechanism, supporting mechanism, base, mounting mechanism, and parallelism adjusting member,
the supporting mechanism, the base, the mounting mechanism, and the parallelism adjusting member being all in two sets,
the supporting mechanism comprising:
a main supporting arm connected to the radial positioning mechanism, and
an auxiliary supporting arm, one end of the auxiliary supporting arm being connected to the main supporting arm and another end of the auxiliary supporting arm being provided with a kink shaft member that is symmetrical about the auxiliary supporting arm; and
the bases connected to the kink shaft members to form revolute pairs with the auxiliary supporting arms.

2. The acoustic emission test sensor fixing device of claim 1, where the radial positioning mechanism comprises an elastomer that connects the main supporting arm to the radial positioning mechanism.

3. The acoustic emission test sensor fixing device of claim 2, where the elastomer comprises a rigid end that connects the main supporting arm to the radial positioning mechanism.

4. The acoustic emission test sensor fixing device of claim 1, where the kink shaft members are inserted into plugholes included on the bases to connect the bases to the kink shaft members to form the revolute pairs.

5. The acoustic emission test sensor fixing device of claim 4, where the bases each comprise a pedestal that includes a bulge that includes the plughole.

6. The acoustic emission test sensor fixing device of claim 1, where the mounting mechanisms each comprise a plugboard that is received in a slot formed in each of the bases to mount the mounting mechanisms to the bases.

7. The acoustic emission test sensor fixing device of claim 1, where the parallelism adjusting members include:
one or more screws, where the main supporting arm receives the one or more screws at a position that corresponds to a position of the bases.

8. The acoustic emission test sensor fixing device of claim 1, where the mounting mechanisms each comprise:
a plugboard that is received by a slot formed in each of the bases, and
a mounting member to mount an acoustic emission test sensor, the mounting member being connected to the plugboard.

9. A device comprising:
a radial positioning mechanism,
a supporting mechanism comprising:
a main supporting arm connected to the radial positioning mechanism, and
an auxiliary supporting arm, one end of the auxiliary supporting arm being connected to the main supporting arm and another end of the auxiliary supporting arm being provided with kink shaft members that are symmetrical about the auxiliary supporting arm;
a base connected to the kink shaft members to form revolute pairs with the auxiliary supporting arm;
a mounting mechanism connected to the base for mounting an object to be tested within the device; and
a parallelism adjusting member connected to the main supporting arm for adjusting a position of the object to be tested within the device.

10. The device of claim 9, where the auxiliary supporting arm forms an acute angle with respect to the main supporting arm.

11. The device of claim 9, where the auxiliary supporting arm forms a right angle with respect to the main supporting arm.

12. The device of claim 9, where the auxiliary supporting arm is hinged to the main supporting arm.

13. The device of claim 9, where the radial positioning mechanism comprises an elastomer that connects the main supporting arm to the radial positioning mechanism.

14. The device of claim 13, where the elastomer comprises a rigid end that connects the main supporting arm to the radial positioning mechanism.

15. The device of claim 9, where one kink shaft, of the kink shaft members, is inserted into a plughole included on the base to connect the base to the kink shaft member to form the revolute pair with the auxiliary supporting arm.

16. The device of claim 15, where the base comprises a pedestal that includes a bulge that includes the plughole, and
where the mounting mechanism comprises a plugboard that is received in a slot formed in the base to mount the mounting mechanism to the base.

17. A method comprising:
connecting a first main supporting arm of a first supporting mechanism to a first end of a radial positioning mechanism and a second main supporting arm of a second supporting mechanism to a second end of the radial positioning mechanism to arrange a first auxiliary supporting arm of the first supporting mechanism and a second auxiliary arm of the second supporting arrangement axis symmetrically with respect to a central line of the radial positioning mechanism;
connecting a first base member to the first auxiliary supporting arm and a second base member to the second auxiliary supporting arm to form a revolute pair for receiving an object to be tested;
mounting, based on a shape of the object to be tested, a quantity of acoustic emission test sensors to the first base member and the second base member;
using a first parallelism adjusting member that is connected to the first main supporting arm and a second parallelism adjusting member that is connected to the second main supporting arm to adjust a position of the object to be tested relative to one or more of the quantity of acoustic emission test sensors.

18. The method of claim 17, further comprising:
testing an acoustic emission test feature of the object to be tested.

19. The method of claim 17, further comprising:
testing an acoustic emission test feature of a damage process of the object to be tested.

20. The method of claim 17, where the object to be tested comprises a rock or a concrete.

* * * * *